US008653130B2

(12) United States Patent
Takemoto et al.

(10) Patent No.: US 8,653,130 B2
(45) Date of Patent: Feb. 18, 2014

(54) COMPOSITIONS CONTAINING SESAMIN-CLASS COMPOUND(S) AND ARACHIDONIC ACID CLASS COMPOUND(S)

(75) Inventors: Daisuke Takemoto, Mishima-gun (JP); Masanori Kontani, Mishima-gun (JP); Yoshiko Ono, Mishima-gun (JP); Yoko Yasutake, Mishima-gun (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 428 days.

(21) Appl. No.: 12/678,637

(22) PCT Filed: Sep. 17, 2008

(86) PCT No.: PCT/JP2008/066767
§ 371 (c)(1),
(2), (4) Date: Mar. 17, 2010

(87) PCT Pub. No.: WO2009/038090
PCT Pub. Date: Mar. 26, 2009

(65) Prior Publication Data
US 2010/0261785 A1  Oct. 14, 2010

(30) Foreign Application Priority Data
Sep. 19, 2007  (JP) .................................. 2007-242864
Mar. 31, 2008  (JP) .................................. 2008-091538

(51) Int. Cl.
*A01N 43/30*  (2006.01)

(52) U.S. Cl.
USPC .......................................................... 514/464

(58) Field of Classification Search
USPC .................................... 546/464; 514/464, 183
See application file for complete search history.

(56) References Cited

U.S. PATENT DOCUMENTS

| 5,180,588 | A | 1/1993 | Shinmen et al. |
| 5,211,953 | A | 5/1993 | Shinmen et al. |
| 5,948,451 | A | 9/1999 | Igarashi |
| 6,159,507 | A | 12/2000 | Igarashi |
| 2002/0039599 | A1* | 4/2002 | Lin et al. ..................... 424/558 |
| 2008/0020033 | A1 | 1/2008 | Kawashima et al. |
| 2009/0054443 | A1 | 2/2009 | Takemoto et al. |
| 2009/0092733 | A1 | 4/2009 | Nakai et al. |
| 2009/0169682 | A1 | 7/2009 | Okumura et al. |
| 2010/0048695 | A1 | 2/2010 | Ono et al. |

FOREIGN PATENT DOCUMENTS

| EP | 0524796 A1 | 1/1993 |
| EP | 2 090 302 | 8/2009 |
| JP | 4-9331 | 1/1992 |
| JP | 5-58902 | 3/1993 |
| JP | 5-194244 | 8/1993 |
| JP | 07-059540 | 3/1995 |
| JP | 2001-139579 | 5/2001 |
| JP | 2004-189619 A | 7/2004 |
| JP | 2008-285463 | 11/2008 |
| WO | 97-01968 | 1/1997 |
| WO | 2005/054415 | 6/2005 |
| WO | 2007/043656 | 4/2007 |
| WO | 2007/105757 | 9/2007 |
| WO | 2007/119378 | 10/2007 |
| WO | 2008/062559 | 5/2008 |
| WO | 2008/126587 | 10/2008 |

OTHER PUBLICATIONS

Shoichi et al, JP63-044843A, published Feb. 25, 1988, Machine Translation used for the Office Action.*
Puri, Prostag Leukotr Ess, 2004, 70, 399-401.*
Liu et al, Nutr Neurosci, 2003, 6(6), 389-392.*
Hemalatha et al, JAOCS, 2004, 81(5), 467-470.*
International Search Report mailed Dec. 16, 2008 in International Application No. PCT/JP2008/066767 filed Sep. 17, 2008.

* cited by examiner

*Primary Examiner* — Jason M Sims
*Assistant Examiner* — Ibrahim D Bori
(74) *Attorney, Agent, or Firm* — Drinker Biddle & Reath LLP

(57) ABSTRACT

A method by which the physiological activities of sesamin-class compounds can be efficiently exhibited and enhanced, as well as an effective compound that can be combined with the sesamin-class compounds to this end. By using sesamin-class compounds in combination with more than specified proportions of arachidonic acid class compounds, the physiological activities of the sesamin-class compounds, for example, their anti-fatigue action is synergistically enhanced to provide compositions that are safe in humans and non-human animals and which hence can be ingested continuously.

8 Claims, 1 Drawing Sheet

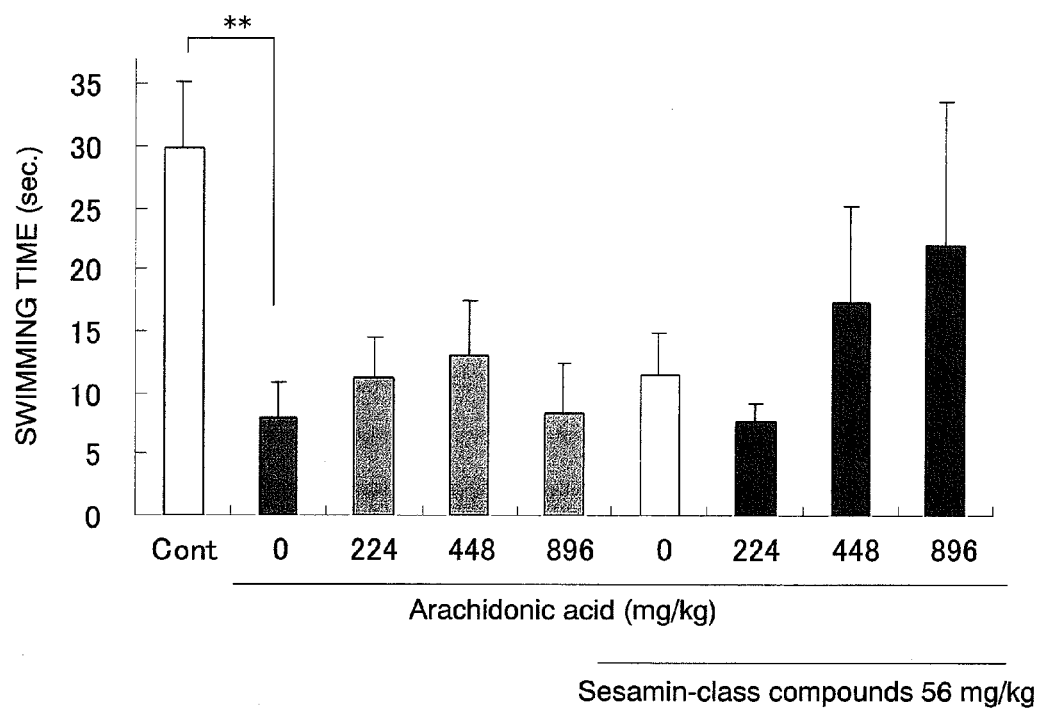
UNDER STRESS FROM SLEEP DEPRIVATION AS A RESULT OF 48-hr IMMERSION IN WATER

COMPOSITIONS CONTAINING SESAMIN-CLASS COMPOUND(S) AND ARACHIDONIC ACID CLASS COMPOUND(S)

CROSS REFERENCE TO RELATED APPLICATIONS

This application is the National Stage of International Application No. PCT/JP2008/066767, filed Sep. 17, 2008, and claims benefit of Japanese patent application no. 2007-242864, filed on Sep. 19, 2007, and Japanese patent application no. 2008-091538, filed Mar. 31, 2008, which are incorporated by reference herein in their entirety.

TECHNICAL FIELD

The present invention relates to compositions containing sesamin-class compound(s) and arachidonic acid class compound(s), more particularly to compositions containing sesamin-class compound(s) and arachidonic acid class compound (s) in specified proportions.

BACKGROUND ART

Sesamin is one of the principal lignan compounds in sesame and is contained in sesame seeds in amounts of 0.1-0.5%. In contrast, episesamin which is an isomer of sesamin does not naturally occur in sesame seeds, but when sesame oil is passed through refining steps (decolorizing and deodorization) to obtain salad oil, sesamin undergoes epimerization to give episesamin as a by-product (Non-Patent Document 1), and sesamin-class compounds refined from the sesame oil are known to contain sesamin and episesamin in proportions of nearly 1:1 by weight ratio (Non-Patent Document 2).

As regards the sesamin-class compounds (hereinafter used as the collective term for sesamin and its analogs; sesamin analogs may be exemplified by episesamin, as well as sesamin, sesaminol, episesaminol, sesamolin, and the like), documents and the like have shown that they have the following physiological activities: the action of inhibiting the metabolism of cholesterol or bile acid in the intestines; the action of alleviating the symptoms of withdrawal from alcohol intoxication; the action of improving hepatic functions; the action of in vivo stabilization of highly unsaturated fatty acids (Patent Document 1); the action of inhibiting Δ5-desaturase; the action of suppressing migraine; the action of inducing apoptosis in human leukemic cells; the action of suppressing the oxidative decomposition of melatonin; the action of ameliorating inflammatory disease (amyotrophic lateral sclerosis); the actions of combating inflammation and protecting against infection; an allergy preventing or ameliorating action by use in combination with oils or fats containing at least one of α-linolenic acid, eicosapentaenoic acid, and docosahexaenoic acid (Patent Document 2); the action of scavenging active oxygen; the action of preventing sickness from drinking; the action of adjusting the balance between omega-6 and omega-3 unsaturated fatty acids (Patent Document 3); the action of suppressing the generation of lipid peroxides; the breast cancer suppressing action; the anti-hypertensive action; the body fat reducing action; and the action of suppressing prostatomegaly by use in combination with saw palmetto.

Patent Document 1: Official Gazette of JP 11-269456 A
Patent Document 2: Official Gazette of JP 5-58902 A
Patent Document 3: Japanese Patent No. 3512196

Non-Patent Document 1: Namiki et al., "Goma-Sono Kagaku to Kinousei (Sesame-Its Science and Functions)", Maruzen Planet Co., Ltd. (1998)
Non-Patent Document 2: Fukuda, Y. et al., J. Am. Oil Chem. Soc., 63, 1027-1031 (1986)

DISCLOSURE OF THE INVENTION

Problems to be Solved by the Invention

As described above, various physiological activities have been reported for sesamin-class compounds, but very few reports have been made about substances that can be used in combination with sesamin-class compounds to enhance their physiological activities. In addition, despite the various physiological activities they have, sesamin-class compounds are precious compounds that are contained in only about 0.1 to 0.5% in naturally occurring sesame seeds; hence, it has been desired to develop a method by which the physiological activities of sesamin-class compounds can be efficiently exhibited and enhanced.

The above-listed Patent Documents 1 to 3 have descriptions about incorporating sesamin-class compounds in highly unsaturated fatty acids to thereby increase the physiological activities of the sesamin-class compounds or stabilize them, but the documents neither disclose nor suggest enhancing the physiological activities of sesamin-class compounds.

An object, therefore, of the present invention is to provide sesamin-class compound containing compositions with enhanced physiological activities. Another object of the present invention is to provide agents that contain sesamin-class compounds as an active ingredient and which have high physiological activities.

Means for Solving the Problems

The present inventors conducted intensive studies with a view to solving the problems mentioned above, and found that by using sesamin-class compounds in combination with more than specified proportions of arachidonic acid class compounds, the physiological activities of the sesamin-class compounds, for example, their anti-fatigue action was markedly increased beyond the range that was predictable from the actions of the sesamin-class compounds alone and those of the arachidonic acid class compounds alone; the present invention has been accomplished on the basis of this finding.

Thus, the present invention relates to the following:
1. A composition containing at least one sesamin-class compound and at least one arachidonic acid class compound, wherein the total weight of the arachidonic acid class compound as calculated for arachidonic acid is at least 8 relative to the total weight of the sesamin-class compound which is taken as unity.
2. The composition as described in 1 above, wherein the total content of the sesamin-class compound is at least 1% of the total weight of the composition.
3. The composition as described in 1 or 2 above, wherein the sesamin-class compound is sesamin, episesamin, or a mixture thereof.
4. The composition as described in any one of 1 to 3 above, wherein the arachidonic acid class compound is arachidonic acid in a free state or a compound which has arachidonic acid as a constituent fatty acid, the compound having arachidonic acid as a constituent fatty acid being an alcohol ester of arachidonic acid or a triglyceride, a phospholipid or a glycolipid, the constituent fatty acids of which are all or partly composed of arachidonic acid.

5. The composition as described in any one of 1 to 4 above, which is for oral use.
6. The composition as described in any one of 1 to 5 above, which is a food or a beverage.
7. An anti-fatigue agent containing at least one sesamin-class compound and at least one arachidonic acid class compound as the active ingredients.
8. Use of a composition containing at least one sesamin-class compound and at least one arachidonic acid class compound for producing an anti-fatigue agent.
9. A method of preventing or treating a fatigue condition, which comprises administering a composition containing at least one sesamin-class compound and at least one arachidonic acid class compound to a subject in need thereof.

Effects of the Invention

Compositions incorporating sesamin-class compound(s) and arachidonic acid class compound(s) are synergistically enhanced in their physiological activities, say, anti-fatigue action, beyond the range that is predictable from the sesamin-class compound(s) and arachidonic acid class compound(s) taken individually, with the result that the compositions have outstanding physiological activities.

The anti-fatigue agents of the present invention have outstanding actions for relieving fatigue and promoting the recovery from fatigue and, what is more, they are safe not only in humans but also in non-human animals and can hence be administered continuously. Therefore, the anti-fatigue agents of the present invention are widely applicable as pharmaceutical compositions including physiologically functional foods.

BRIEF DESCRIPTION OF THE DRAWINGS

FIG. 1 is a graph showing the result of the animal experiment conducted with mice in Example 1, in which compositions containing sesamin-class compounds and arachidonic acid class compounds exhibited an anti-fatigue action in the animals that ingested them.

BEST MODE FOR CARRYING OUT THE INVENTION

Sesamin-Class Compounds

The term "sesamin-class compound" of the present invention is the collective term for a series of compounds including sesamin and its analogs. Examples of the above-mentioned sesamin analogs include not only episesamin but also the dioxabicyclo[3.3.0]octane derivatives mentioned in JP 4-9331 A. Specific examples of the sesamin-class compound include sesamin, sesaminol, episesaminol, sesamolin, etc. and stereoisomers or racemic bodies of these compounds may be used either alone or in admixture. In the present invention, sesamin, episesamin or mixtures thereof are preferably used. In addition, the metabolites of sesamins (such as those described in JP 2001-139579 A) may be used in the present invention as the sesamin analogs included in the category of sesamin-class compounds of the present invention on the condition that they exhibit the effects of the present invention.

The sesamin-class compounds to be used in the present invention are not limited in any way by their form, production methods, and the like. If, for example, sesamin is chosen as the sesamin-class compound, sesame oil may be subjected to extraction by a known method (such as the one described in JP 4-9331 A) to obtain sesamin (hereinafter called a sesamin extract or concentrate), which is then used. If desired, a commercial grade of sesame oil (in liquid form) may be used as such. However, one disadvantage of using sesame oil is its low sesamin content (usually less than 1%), so if one attempts to incorporate sesamin in the amount required to attain its physiological activity, the volume per unit dosage of the arachidonic acid class compound containing composition to be prescribed becomes so excessive as to cause occasional inconvenience to ingestion. In particular, in the case where the composition is formulated for oral administration, the preparation (e.g. tablet or capsule) becomes so bulky as to cause trouble in ingestion. Hence, for the specific reason that the composition need be ingested in a smaller amount, the sesamin extract (or purified sesamin) from sesame oil is preferably used. It should be noted here that since the characteristic flavor of sesame oil is sometimes evaluated to be organoleptically undesirable, the sesamin extract (or sesamin concentrate) may be rendered tasteless and odorless by a known means such as treatment with activated clay.

Thus, the sesamin-class compounds that are preferably used are the concentrates of sesamins that are enriched in the concentration of sesamin-class compounds by extraction and/or purification from materials originating from foods such as sesame oil. The content may be set as appropriate for the kind of sesamin-class compounds to be used or the form of the composition in which the sesamin-class compounds are to be incorporated; typically used concentrates of sesamin-class compounds are such that the sesamin-class compounds have been enriched to a total content of at least 1% of the total weight of the composition. The total content of sesamin-class compounds in their concentrate is preferably at least 20 wt %, more preferably at least 50 wt %, more preferably at least 70 wt %, and most preferably at least 90 wt %.

Arachidonic Acid Class Compounds

The ingredient effective in enhancing the physiological activity of sesamin-class compounds is arachidonic acid, and as this arachidonic acid, arachidonic acid in a free state or all compounds that have arachidonic acid as a constituent fatty acid may be used either alone or in admixture. The arachidonic acid in a free state and all compounds that have arachidonic acid as a constituent fatty acid are herein called "arachidonic acid class compounds." The compounds that have arachidonic acid as a constituent fatty acid are in no way limited and include arachidonic acid salts (e.g., calcium salt and sodium salt), lower alcohol esters of arachidonic acid (e.g., methyl ester of arachidonic acid and ethyl ester of arachidonic acid), as well as triglycerides, phospholipids and glycolipids, the constituent fatty acids of which are all or partly composed of arachidonic acid.

As described above, arachidonic acid is the active ingredient that enhances the physiological activity of the sesamin-class compounds, so it is preferred to use arachidonic acid class compounds with a higher content of arachidonic acid; for example, the above-mentioned arachidonic acid containing triglycerides (synonymous with triglycerides that contain arachidonic acid in part or all of the constituent fatty acids, or with oils or fats that contain such triglycerides) include oils or fats (triglycerides) in which arachidonic acid accounts for at least 10 wt % (w/w), preferably at least 20 wt % (w/w), more preferably at least 30 wt % (w/w), and most preferably at least 40 wt % (w/w), of all fatty acids that constitute the triglyceride. Such arachidonic acid containing triglycerides can industrially be produced by, for example, cultivating microorganisms capable of producing arachidonic acid containing oils or fats (triglycerides); commercial examples include a microorganism oil containing 25 mass % of arachidonic acid (containing 95% or more of triglyceride) and available from SUNTORY LIMITED. under the name of SUNTGA (registered trademark) 25 and a microorganism oil containing 40 mass % of arachidonic acid (containing 95% or more of triglyceride) and also available from SUNTORY LIMITED. under the name of SUNTGA (registered trademark) 40S; the desired arachidonic acid containing triglycerides can also be produced by cultivating microorganisms capable of producing arachidonic acid containing oils or fats (triglycerides) by the methods and under the conditions that are described in JP 2003-48831 A, JP 2006-83136 A, and WO 2003/004667. The microorganisms and culture conditions that can specifically be employed are described in the above-mentioned references in detail.

Compositions Incorporating Sesamin-Class Compound(s) and Arachidonic Acid Class Compound(s)

The compositions of the present invention, on account of their containing the above-descried sesamin-class compound(s) together with more than the specified proportion of the arachidonic acid class compound(s), can provide synergistic enhancement of the physiological activities (say, anti-fatigue action) of sesamin-class compounds. The compositions of the present invention can also be utilized as foods and beverages having high anti-fatigue action.

The total proportion of sesamin-class compound(s) as incorporated in the compositions of the present invention (e.g., pharmaceutical compositions, foods or beverages, and the like) that also contain arachidonic acid class compound(s) is typically at least 1 wt %, preferably from 1 to 50 wt %, and more preferably from 1 to 10 wt %. The total proportion of arachidonic acid class compound(s) as incorporated in the compositions is not limited in any particular way, as long as it is within the range over which their effectiveness in synergistically enhancing the above-described physiological activities of sesamin-class compound(s) is exhibited, and it may be chosen as appropriate for such conditions as the form of the compositions and the pathological condition to be treated; arachidonic acid class compound(s) are typically incorporated in 0.001 to 50 wt %, preferably 0.01 to 40 wt %, more preferably 0.05 to 40 wt %, and most preferably 0.1 to 30 wt %, relative to the total quantity of the composition. Note that the amounts of arachidonic acid class compound(s) are indicated herein in terms of the values as calculated for arachidonic acid.

Generally, sesamin class compounds are ingested by adults preferably in a dose of 1 to 200 mg, more preferably about 5 to 100 mg, per day. The daily intake of arachidonic acid class compounds is generally from 10 to 900 mg, preferably from 50 to 700 mg, and more preferably from 100 to 500 mg in terms of the values as calculated for arachidonic acid.

Depending on their total weight, the compositions of the present invention can incorporate sesamin-class compounds typically in amounts of 1 to 100 mg, preferably 1 to 60 mg, and more preferably about 3 to 60 mg. The compositions can also incorporate arachidonic acid class compounds typically in amounts of 10 to 900 mg, preferably 50 to 700 mg, and more preferably about 100 to 500 mg.

In the experiments conducted by the present inventors using fatigue animal models, which will be explained below in detail, administering 56 mg/kg of sesamin-class compounds (the amount of sesamin-class compounds (mg) per kg of the body weight of an animal model) together with 448 mg/kg and more of arachidonic acid class compounds caused a marked enhancement of the anti-fatigue action over the case where only sesamin-class compounds were administered in 56 mg/kg or only arachidonic acid class compounds were administered in 448 mg/kg. When 56 mg/kg of sesamin-class compounds were administered together with 224 mg/kg of arachidonic acid class compounds, there was no enhancement of the anti-fatigue action (see FIG. 1). Hence, the specified proportion of arachidonic acid class compounds at which their effectiveness in synergistically enhancing the physiological activities of sesamin-class compounds is exhibited is such that the total weight of arachidonic acid class compounds is at least 8, preferably at least 10, and more preferably at least 15, with the total weight of sesamin-class compounds being taken as unity.

In addition to the sesamin-class compounds and arachidonic acid class compounds, the compositions of the present invention may incorporate any optional ingredients to an extent that will not impair the effects of the compositions. For example, physiologically active ingredients such as vitamins (e.g., vitamin E and vitamin C), minerals, hormones, nutritional ingredients and flavoring agents, as well as additives that are commonly incorporated in the formulation procedure, such as emulsifiers, tonicity agents (isotonization agents), buffers, dissolution promoters, antiseptics, stabilizers and antioxidants, may be incorporated as appropriate.

Since the compositions of the present invention provide an anti-fatigue action as enhanced synergistically by incorporating sesamin-class compounds and arachidonic acid class compounds, they can also be utilized as health foods with advantage. Examples of health foods as referred to hereinafter include preparations or foods, such as capsules and tablets, in which the composition of the present invention itself that incorporates sesamin-class compounds and arachidonic acid class compounds is contained as the active ingredient, as well as physiologically functional foods (foods for specified health use or FOSHU, and qualified FOSHU) wherein the composition is incorporated into common foods as one ingredient so that the foods are provided with various actions including the anti-fatigue action to the living body. Also included in the category of the composition of the present invention are foods that are characterized by having the anti-fatigue action and which have a label attached thereto indicating that they relieve the fatigue in the living body or promote recovery from the fatigue.

The form of the foods and beverages that contain sesamin-class compounds and arachidonic acid class compounds is not limited in any particular way, and they may be formulated in any desirable forms including, for example, solid forms such as powdery, granular or tablet forms, liquid forms such as solution, emulsion or dispersion forms, and semisolid forms such as a paste form.

The compositions of the present invention can also be utilized as pharmaceutical compositions. In this case, the compositions of the present invention may be formulated in dosage forms such as liquids, tablets, granules, powders, capsules, dry syrups or pills, and administered perorally; alternatively, they may be formulated as an injection for administration. The mode of administration can be chosen as appropriate for the pathological condition, its progress, and other conditions.

Anti-Fatigue Action and Anti-Fatigue Agents

The compositions of the present invention are also useful as anti-fatigue agents in humans and non-human animals. The term "non-human animals" as used herein refers to any animal which is a subject to receive anti-fatigue treatment. Especially, the compositions are used to industrial animals, pets, and laboratory animals. It is especially preferred to use the compositions to humans. The term "industrial animals" refers to farm animals such as cattle, horse, swine, goat, sheep, etc., as well as racehorses, hunting doges, etc.; the term "pets" refers to dog, cat, marmoset, hamster, etc.; the term "laboratory animals" refers to mouse, rat, guinea pig, beagle, miniature pig, rhesus monkey, crab-eating monkey, and other animals that are subjected to research in such fields as medicine, biology, agronomy, pharmacy, etc. The anti-fatigue agents of the present invention are used in humans, industrial animals, pets and laboratory animals that perceive fatigue, and they are used with particular advantage in humans.

Fatigue as appears here is a temporary lowering of physical or mental performance that results from continued application of a physical or mental stress, and lowered performance means a drop in the quality or quantity of a physical or mental working capacity. It should also be noted that the term "fatigue" as used herein covers chronic fatigue syndrome and death by overwork.

The anti-fatigue agents of the present invention are those agents which have an action for attenuating the above-defined fatigue or achieving recovery from it, as specifically described by the following effects: prolonging the duration for which a moving or acting site (including the brain) keeps functioning, and suppressing the increase in fatigue-causing substances given the same amount of motion or action (improvement of stamina and increase of body strength); or ameliorating such a condition that the brain or nerves have come to perceive fatigue although a moving or acting site is yet to get tired, and promoting the recovery of the moving or acting site from the tired state to the normal state.

Chronic fatigue syndrome which is to be treated with the anti-fatigue agents of the present invention means general symptoms such as systemic feelings of weariness (tiredness) and malaise (lassitude), slight fever, lymph node dilation, muscle pain, joint pain, and psychoneurotic symptoms, all being so prolonged as to potentially interfere with the daily life of the affected individual. The anti-fatigue agents of the present invention are capable of treating chronic fatigue syndrome; in other words, they can palliate the various symptoms of chronic fatigue syndrome such that the affected individual is brought to the normal condition. Death by overwork which is also to be treated with the anti-fatigue agents of the present invention means such a condition of individuals who are under too extreme fatigue to be capable of keeping physical vigor and yet they cannot fully perceive fatigue, with the result that cerebrovascular disease or cardiac disease manifests itself, causing the individuals to become permanently unable to work or bringing them to death. The anti-fatigue agents of the present invention are capable of treating chronic fatigue syndrome, whereby they can prevent death from overwork. The anti-fatigue action in the present invention, or its effectiveness as "anti-fatigue agents" can be verified by such a method as measuring the swimming time in a water immersion sleep deprivation test. Mice that have been kept in an environment such as water immersion where they are unable to have a good sleep or take a rest position so they cannot have a physical or mental rest are forced to swim under a weight load, and the critical swimming time (i.e., the time it takes for the mouse to have its nose finally submerged in the water (and incapable of rising up to its surface again)) is measured to confirm the degree of their fatigue. Since this is an animal model for physical or mental fatigue, an extension of the critical swimming time as achieved by administering it with the test substance means the verification of resistance to fatigue, as exemplified by prevention or relief of physical and/or mental fatigue or any accompanying pains including muscle pains, a sufficient increase in body strength to extend the time to total exhaustion, and maintenance of physical vigor in the tired model.

The anti-fatigue agents of the present invention have the advantage that one who ingests them will not easily get tired, and they are also effective in achieving recovery from fatigue. To be more specific, if one feels a physical fatigue after having a muscular exercise as in sports, or feels a mental fatigue after performing a continuous task such as calculation, they may ingest the anti-fatigue agent of the present invention to recover from the fatigue; if they ingest the anti-fatigue agent before working or sporting, they can be prevented from getting tired. If the anti-fatigue agent is ingested before or during sporting, it is expected to improve stamina. As a further advantage, mental fatigue as well as diseases that accompany it can also be prevented by ingesting the anti-fatigue agent on a regular basis.

The anti-fatigue agents of the present invention may be administered perorally in various forms including liquids, tablets, granules, powders, capsules, dry syrups, pills and the like; they may also be administered in such a form as injection; the mode of administration can be chosen as appropriate for the pathological condition, its progress, and other conditions.

If desired, two preparations, one containing the sesamin-class compound(s) and the other containing the arachidonic acid class compound(s), may be formulated separately and then administered almost simultaneously or, alternatively, one preparation may be first administered and while its effect persists, the other preparation is administered; in this way, an enhancement of the anti-fatigue action of sesamin-class compounds as intended by the present invention can be achieved. Hence, a kit comprising two preparations, one containing sesamin-class compound(s) and the other containing arachidonic acid class compound(s), is also included in the scope of the anti-fatigue agents of the present invention.

EXAMPLES

The present invention is described in greater detail by means of the following examples, to which the present invention is in no way limited.

Example 1

Anti-Fatigue Effect From Arachidonic Acid Class Compounds and Sesamin-Class Compounds A sesamin/episesamin mixture (sesamin:episesamin=5:5 in weight ratio) was used as sesamin-class compounds under test, and SUNTGA (registered trademark) 40S (oil or fat containing 48% arachidonic acid) was used as arachidonic acid class compounds. Note that SUNTGA (registered trademark) 40S was produced by the method described in Example 1 of JP 2003-48831 A.

The anti-fatigue action was evaluated by a water immersion sleep deprivation test. The evaluation was conducted in accordance with the following partial modification of the method of Tanaka et al. (Neuroscience, Let. 352, 159-162, 2003.) Balb/c male mice (5-week old) as test animals were purchased from Japan SLC, Inc. and conditioned in a test environment for a week, and the animals that have grown normally were subjected to the test. They were divided into nine groups such that each group consisted of 3 to 10 animals and had the same average body weight; the mice in the respective groups were kept for two weeks. During the 2-week breeding period, the mice were fed a standard diet for laboratory animals (AIN-93G of Oriental Yeast Co., Ltd.) as mixed with test substances in amounts that would give the intakes indicated in Table 1 below. Thereafter, eight out of the nine test groups (groups 2 to 9) were designated as water immersion groups under stress from sleep deprivation, which were kept in breeding cages, not on paper chips but in tap water (23° C.) supplied to a depth of 7 mm, thereby depriving the mice of sleep. During sleep deprivation under immersion in water, the mice were fed the standard diet for laboratory animals (AIN-93G of Oriental Yeast Co., Ltd.) and the animals in three groups (groups 3 to 5) were forcibly administered with the above-described arachidonic acid containing oil or fat as dissolved in olive oil (arachidonic acid groups kept under immersion in water), whereas the animals in group 6 were administered orally with the above-described sesamin/episesamin mixture as dissolved in olive oil (sesamin-class compound group kept under immersion in water); the oral administration was performed for two days on a one-dose-a-day basis. Three groups (groups 7 to 9) were administered orally, again for two days on a one-dose-a-day basis, with the above-described arachidonic acid containing oil or fat and the above-described sesamin/episesamin mixture as dissolved in olive oil (arachidonic acid+sesamin-class compound groups kept under immersion in water). The control group (group 2) was administered orally with olive oil. The remaining group (group 1) was kept in a breeding cage where paper chips were laid down, as the animals were administered orally with olive oil for two days on a one-dose-a-day basis (normally kept control group). The doses of sesamin-class compounds and arachidonic acid as administered to the respective groups during sleep deprivation under immersion in water are shown in Table 1. The values indicated in Table 1 for the amount of arachidonic acid administered are based on the dose of the administered arachidonic acid containing oil or fat as calculated for arachidonic acid; the values for the dose of sesamin-class compounds were calculated as the sum of sesamin and episesamin.

After two days of keeping under immersion in water or normal keeping, each mouse was fitted with a weight at the tail which corresponded to 8% of its body weight, and was allowed to swim in a water tank of 18 cmϕ that was filled with water to a depth of 30 cm; the time it took for each mouse to have its nose finally submerged in the water (until it would not rise up to the surface again) was measured as the critical swimming time. The critical swimming time of the mice in the groups kept under immersion in water (under stress from deprivation of sleep) was shorter than that of the mice in the normally kept group. The degree by which the administration of the test samples (arachidonic acid+sesamin-class compounds) could suppress the shortening of the critical swimming time was measured to evaluate the anti-fatigue action of the test samples.

TABLE 1

| Group 1 | (Cont) Normally kept control group | Olive oil |
| Group 2 | Control group kept under immersion in water | Olive oil |
| Group 3 | Arachidonic acid group kept under immersion in water | Arachidonic acid in 224 mg/kg/day (in olive oil) |
| Group 4 | Arachidonic acid group kept under immersion in water | Arachidonic acid in 448 mg/kg/day (in olive oil) |
| Group 5 | Arachidonic acid group kept under immersion in water | Arachidonic acid in 896 mg/kg/day (in olive oil) |
| Group 6 | Sesamin-class compound group kept under immersion in water | Sesamin in 56 mg/kg/day (in olive oil) |
| Group 7 | Arachidonic acid + sesamin-class compound (4:1) group kept under immersion in water | Arachidonic acid in 224 mg/kg/day + sesamin-class compounds in 56 mg/kg/day (in olive oil) |
| Group 8 | Arachidonic acid + sesamin-class compound (8:1) group kept under immersion in water | Arachidonic acid in 448 mg/kg/day + sesamin-class compounds in 56 mg/kg/day (in olive oil) |
| Group 9 | Arachidonic acid + sesamin-class compound (16:1) group kept under immersion in water | Arachidonic acid in 896 mg/kg/day + sesamin-class compounds in 56 mg/kg/day (in olive oil) |

The results are shown in FIG. 1 (wherein ** represents significant differences at a risk factor of less than 1% in a Student's t-test). As is clear from FIG. 1, the swimming time of the control group kept under immersion in water was significantly shorter than that of the normally kept control group. On the other hand, the effectiveness in suppressing the shortening of the swimming time was observed in all groups that were administered with only arachidonic acid as the test sample in 224 mg/kg to 896 mg/kg and in the group that was administered with only sesamin-class compounds as the test sample in 56 mg/kg. In the groups administered with arachidonic acid and sesamin-class compounds simultaneously in combination, no effectiveness was observed for suppressing the shortening of the swimming time when the ratio of arachidonic acid to sesamin-class compounds was 4:1, but a strong effect for suppressing the shortening of the swimming time was observed at ratios of 8:1 and 16:1, thus verifying the synergistic enhancement of the anti-fatigue action.

Example 2

Formulations

Formulation 1: Preparation of Capsules

Gelatin (product of Nitta Gelatin, Inc.) and glycerol as a food additive (product of Kao Corporation) were mixed at a weight ratio of 100:35; then, water was added to the mixture and by dissolving in a temperature range of 50 to 60° C., a gelatin coat having a viscosity of 2000 cp was prepared. In the next step, 83 wt % of SUNTGA (registered trademark) 40S (SUNTORY LIMITED.), 3 wt % of α-tocopherol, and 14 wt % of wheat germ oil were mixed intimately, followed by addition of 1.4 wt % of sesamin and subsequent stirring to prepare contents 1. In a separate step, 28 wt % of SUNTGA (registered trademark) 40S (SUNTORY LIMITED.), 3 wt % of α-tocopherol, and 69 wt % of wheat germ oil were mixed intimately, followed by addition of 1.4 wt % of sesamin and subsequent stirring to prepare contents 2. Using the thus prepared gelatin coat and two kinds of contents, capsule molding and drying were performed in the usual manner to produce soft capsules each containing 180 mg of the fill. Each of the soft capsules was suitable for oral ingestion.

Formulation 2: Use in Juice

SUNTGA (registered trademark) 25S (SUNTORY LIMITED.), vitamin E oil, sesamin, and soybean lecithin (Tsuji Oil Mill Co., Ltd.) were mixed at a weight ratio of 8:0.9:0.1:1 and the mixture was dispersed in water uniformly to prepare a liposome dispersion. The liposome dispersion was added to orange juice, carbonated water, coffee beverage, milk, soybean milk or instant thick soup in one-hundredth the volume of these bases to prepare the associated beverages, which are the foods or beverages of the present invention. All of these foods or beverage were suitable for oral ingestion.

The invention claimed is:

1. A composition comprising at least one sesamin-class compound and at least one arachidonic acid class compound, wherein a ratio of a total weight of the arachidonic acid class compound as calculated for arachidonic acid to a total weight of the sesamin-class compound is 8:1 to 16:1, wherein the sesamin-class compound is sesamin, episesamin, or a mixture thereof, and wherein the arachidonic acid class compound is arachidonic acid in a free state or an ester thereof.

2. The composition according claim 1, wherein the ester is a lower alcohol ester of arachidonic acid or a triglyceride.

3. The composition according to claim 1, which is for oral use.

4. The composition according to claim 1, which is a food or a beverage.

5. A method of treating fatigue, comprising administering an anti-fatigue composition comprising at least one sesamin-class compound and at least one arachidonic acid class compound to a subject in need of the treatment, wherein a ratio of a total weight of the arachidonic acid class compound as calculated for arachidonic acid to a total weight of the sesamin-class compound is 8:1 to 16:1, wherein the sesamin-class compound is sesamin, episesamin, or a mixture thereof, and wherein the arachidonic acid class compound is arachidonic acid in a free state or an ester thereof.

6. The method according claim 5, wherein the ester is a lower alcohol ester of arachidonic acid or a triglyceride.

7. The method according to claim 5, wherein the composition is administered orally.

8. The method according to claim 5, wherein the composition is a food or a beverage.

* * * * *